(12) United States Patent
Gunning et al.

(10) Patent No.: US 7,718,792 B2
(45) Date of Patent: May 18, 2010

(54) STEREOSPECIFIC REDUCTION OF SAPOGEN-3-ONES

(75) Inventors: Philip James Gunning, Godmanchester (GB); Peter David Tiffin, Godmanchester (GB)

(73) Assignee: Phytopharm PLC, Cambridgeshire (GB)

( * ) Notice: Subject to any disclaimer, the term of this patent is extended or adjusted under 35 U.S.C. 154(b) by 692 days.

(21) Appl. No.: 10/531,086

(22) PCT Filed: Apr. 28, 2003

(86) PCT No.: PCT/GB03/01780

§ 371 (c)(1),
(2), (4) Date: Jun. 21, 2005

(87) PCT Pub. No.: WO2004/037845

PCT Pub. Date: May 6, 2004

(65) Prior Publication Data

US 2006/0041119 A1 Feb. 23, 2006

(30) Foreign Application Priority Data

Oct. 28, 2002 (GB) ................................. 0225106.4
Jan. 22, 2003 (GB) ................................. 0301505.4

(51) Int. Cl.
*C07J 71/00* (2006.01)
(52) U.S. Cl. ...................................................... 540/17
(58) Field of Classification Search ....................... None
See application file for complete search history.

(56) References Cited

U.S. PATENT DOCUMENTS

| 3,875,195 A | 4/1975 | Nickolson |
| 5,703,052 A | 12/1997 | Deninno |
| 5,807,834 A | 9/1998 | Morehouse |
| 5,939,398 A | 8/1999 | Deninno |
| 6,150,336 A | 11/2000 | Deninno |

FOREIGN PATENT DOCUMENTS

| GB | 736818 | 9/1955 |
| GB | 763301 | 12/1956 |
| WO | WO-99/48482 | 9/1999 |
| WO | WO-99/48507 | 9/1999 |
| WO | WO-01/23406 | 4/2001 |
| WO | WO-01/49703 | 7/2001 |
| WO | WO-02/079221 | 10/2002 |
| WO | WO 02079221 A | 10/2002 |

OTHER PUBLICATIONS

Jantzen and Robinson, Modern Pharmaceutics, 1996, p. 596.*
March, J. Advanced Organic Chemistry, 1992, pp. 360-362.*
Smith et al. Oxford Dictionary of Biochemistry and Molecular Biology, 1997, p. 584.*
Yashin et al. Journal of the Chemical Society, 1951, 73, 4654-57.*
Djerash et al.. Journal of the American Chemical Society, 1953, 75(20), 4885-87.*
Helv. Chim. Acta. 66(1983) 192-217.
Brown et al. J. Am. Chem. Soc. 94 (1972) 7159-7161.
Steroids 45 (1985) 39-51.
J. Chem. Soc. Commun. (1982) 1239-1240.
Tetrahedrom 40 (1984) 851-854.
Tetrahedrom 45 (1989) 3717-3730.
Marker et al. J. Am. Chem. Soc. 62 (1940) 2525.
Marker, R.E. et al. 'Sterols. LVI. Sarsasapogenin derivatives. Episarsasapogenin' J. Am. Chem. Soc. 61(1939) 943-944.
J. Nat. Prod. 42(1979) 478-482.
Onderstepoort J. Vet. Res. 61(1994) 351-359.
Lajis Nordin, H. et al. 'Epi-sarsasapogenin and epi-smilagenin: Two sapogenins isolated from the rumen content of sheep intoxicated by Brachiaria decumbens' Steroids 58 8 (1993) 387-389.
Bungaard, H. 'Advanced Drug Delivery Reviews' 8(1992) 1-38.
Kakeya, N. et al. Chem. Pharm. Bull. 32 (1984) 692.
Morita, K. 'Studies on the Sapogenins of Dioscorea tokoto Makino. III. Synthesis of Isohodeasapogenin and Some Reactions of Tokorogenin' Bulletin of the Chemical Society of Japan 32 8(1959) 796-799.
Morita, K. 'Studies on the Sapogenins of Dioscorea tokoto Makino. III. The Structure of Tokorogenin' Bulletin of the Chemical Society of Japan 32 8(1959) 791-795.
Chang, F.C. et al. 'Acylamides as Epimerization Reagents' J. Am. Chem. Soc. 80(1958) 2906.
Drogemuler, Michael et al. 'Steroidal pyrazines, synthetic advances and biological activity' Proceedings of ECSOC-2: The second international electronic conference on synthetic organic chemistry 1998 (1999) 209-225.
Gobbini M. et al. 'Digitalis-like compounds: synthesis and biological evaluation of 3beta-(aminoalkylthio) derivatives' Bioorganic and Medicinal Chemistry Letters 7 4 469-472.
Babcock, J.C. et al. 'Reductive Methylation of Steroid Ketones' J. Am. Chem. Soc 74 (1952) 5472-5474.

(Continued)

*Primary Examiner*—James O Wilson
*Assistant Examiner*—Noble Jarrell
(74) *Attorney, Agent, or Firm*—Husch Blackwell Sanders LLP Welsh & Katz

(57) ABSTRACT

A method to stereospecifically prepare a steroidal sapogenin or a derivative thereof by reducing a 3-keto,5β-H steroidal sapogenin with a hindered organoborane or an organo-aluminium hydride. A 3β-hydroxy,5β-H steroidal sapogenin or derivative thereof may be prepared by reducing the 3-keto, 5β-H steroidal sapogenin using as reducing agent a relatively highly hindered organoborane reagent or by SN 2 inversion of a 3α-hydroxy,5β-H steroidal sapogenin or derivative thereof. The organo-aluminium hydride may be used to prepare a 3α,5β-H steroidal sapogenin or derivative thereof. The invention provides a convenient route to useful steroidal sapogenins such as sarsasapogenin, episarsasapogenin, smilagenin, epismilagenin and esters thereof, from readily available or easily preparable starting materials (e.g. diosgenone, preparable from diosgenin).

24 Claims, No Drawings

OTHER PUBLICATIONS

Tochtrop, Gregory P. et al. 'Synthesis of '3,4-(13)c(2)!-enriched bile salts as NMR probes of protein-ligand interactions' The Journal of Organic Chemistry 67 19 6764-6771.

Weet, J.F. et al. 'Mineralcorticoid properties of potential metabolites of 18-hydroxydeoxycorticosterone and 18-hydroxyprogestrone' J. Med. Chem. 28 2 (1985) 233-239.

Steroids 36 (1980) 299-303.

J. Agric. Food Chem. 41 (1993) 914-917.

J. Am. Chem. Soc. 74 (1952) 422-424.

Journal of Pharmaceutical Sciences 77 (1988) 285.

Rouessac et al. 'Une voie d'acces a la trimethyl-4, 4, 7a-tetrahydro-3a.alpha.,4,7,7a.alpha.(3H)-benzofuranone-2 a partir des alcoxy-5 tri-methyl-4, 4, 7a-hexhydro 3a.alpha.,4,5,6,7a.alpha.(3H)-benzofuranones-2' Bulletin de la Societe Chimique de France 2 5-6(1981) 199-203.

M.P. Irismetoc, M.I. Goryaev. Modified Steriods. IX. Sythesis of A/B-cis-and A/B-trans-Derivatives and Study of PMR Spectra in the Series of Diogenine Steriod Compound UDC 541.63+547.92.

* cited by examiner

US 7,718,792 B2

STEREOSPECIFIC REDUCTION OF SAPOGEN-3-ONES

FIELD OF THE INVENTION

The present invention relates to stereospecific synthesis of 3-hydroxy-5β-H steroidal sapogenins and their derivatives.

BACKGROUND OF THE INVENTION

It has been shown that certain sapogenins and their derivatives (more particularly, sapogenins possessing a 5β hydrogen atom, and most particularly compounds possessing a 3-hydroxy group and a 5β-hydrogen atom, such as sarsasapogenin, episarsasapogenin, smilagenin and epismilagenin) have utility in the treatment of cognitive dysfunction and other conditions. Such activity is described, for example, in WO-99/48482, WO-99/48507, WO-01/49703, WO-02/079221 and WO-01/23406, the disclosures of which are incorporated herein by reference. The scheme for naming of the ring system and the carbon positions used herein is as given in these prior publications.

The literature describes methods for the synthesis of 3-hydroxy steroids and 3-hydroxy steroidal sapogenins. For example, the synthesis of 3β-hydroxy-5α-H steroids from the corresponding 3-keto-5α-H steroids has been effected with sodium borohydride in tetrahydrofuran and methanol or by using lithium aluminium hydride in diethyl ether (*Helv. Chim. Acta*, 66, 192-217 (1983)).

U.S. Pat. No. 3,875,195 (1975), the disclosure of which is incorporated herein by reference, describes the catalytic reduction of 3-keto-5β-H steroids to 3β-hydroxy-5β-H steroids in a lower carboxylic acid with Raney nickel and hydrogen under pressure. These workers note that the Meerwein-Ponndorf-Verley (MPV) reduction leads to mixtures of 3α-and 3β-hydroxy steroids in equal portions. The separation of such mixtures is reported to be difficult.

Since the introduction of the family of highly hindered trialkylborohydride reducing agents, commonly known as Selectrides®, beginning in the early 1970s (Brown et al., *J. Am. Chem. Soc.* 94, 7159-7161 (1972)), a number of publications have appeared in which these reducing agents have been applied to certain sterol synthetic methods. For example, in *Steroids*, 36, 299-303 (1980), *Steroids*, 45,39-51 (1985), *J. Chem. Soc. Commun.* 1239-1240 (1982), *Tetrahedron*, 40, 851-854 (1984), *Helv. Chim. Acta*, 66, 192-217 (1983), U.S. Pat. No. 6,150,336 (2000), and *Tetrahedron*, 45, 3717-3730 (1989), the disclosures of which are incorporated herein by reference, stereospecific selectride reductions of certain 3-keto-5β and 3-keto-5α steroids to their respective 3β-OH, 5β-H and 3α-OH,5α-H sterols are described.

In relation to steroidal sapogenins, the art describes the synthesis of smilagenin by reduction of smilagenone with aluminium isopropoxide in isopropyl alcohol, the MPV reduction (Marker et al, *J. Amer. Chem. Soc.*, 62, 2525 (1940)). Marker has reported the MPV reduction of sarsasapogenone to afford a mixture of sarsasapogenin and episarsasapogenin (Marker and Rohrmann, *J. Amer. Chem. Soc.*, 61, 943 (1939)). The disclosures of these publications are incorporated herein by reference.

The art has also reported certain catalytic hydrogenations, as exemplified by Blunden's preparation of epitigogenin from tigogenone using hydrogenation over an Adams catalyst (platinum (IV) oxide) in glacial acetic acid containing 2% hydrochloric acid (*J. Nat. Prod.* 42, 478-482 (1979); *Onderstepoort J. Vet. Res.*, 61, 351-359 (1994)). Marker has reported the hydrogenation of sarsasapogenone using Adams catalyst in ethanol to afford episarsasapogenin (Marker and Rohrmann, *J. Amer. Chem. Soc.*, 61, 943 (1939)). The art has also reported sodium borohydride reduction, as exemplified by Miles's preparation of episarsasapogenin from sarsasapogenone using sodium borohydride (*J. Agric. Food Chem.*, 41, 914-917 (1993)). The art has also reported lithium aluminium hydride reduction, as exemplified by Djerassi's preparation of epismilagenin from smilagenone (*J. Am. Chem. Soc.*, 74, 422-424, (1952)) and Lajis's preparation of episarsasapogenin from sarsasapogenone (*Steroids*, 58, 387-389 (1993)). The disclosures of these publications are incorporated herein by reference.

U.S. Pat. No. 5,703,052 (1997), U.S. Pat. No. 5,807,834 (1998) and U.S. Pat. No. 5,939,398 (1999), the disclosures of which are incorporated herein by reference, report methods for the synthesis of 3α-hydroxy-5α-H sapogenins using K-Selectride® at low temperatures.

WO-02/079221 (published 10 Oct. 2002), describes in Example 6, a synthesis of episarsasapogenin by reduction of sarsasapogenone using lithium tri-tert-butoxyaluminohydride. However, this publication is not prior art in all countries.

The present invention seeks to provide an improved stereospecific synthesis of 3-hydroxy-5β-hydrogen steroidal sapogenins, and more preferably the 3β-hydroxy, 5β-H-sapogenins defined and described in the said publications WO-99/48482, WO-99/48507, WO-01/49703, WO-02/079221 and WO-01/23406, as well as their derivatives such as, for example, the corresponding saponins and other physiologically acceptable forms such as salts and esters, which may serve as pro-drugs.

In a most preferred embodiment, the present invention seeks to provide an efficient stereospecific synthesis of sarsasapogenin, smilagenin, episarsasapogenin, epismilagenin and their pro-drugs and other physiologically acceptable forms.

BRIEF DESCRIPTION OF THE INVENTION

The present invention provides in a first aspect a method of stereospecifically preparing a 3-hydroxy-5β-H steroidal sapogenin or a derivative thereof, which comprises reducing a 3-keto-5β-H steroidal sapogenin using a reducing agent comprising a hindered organoborane or an organo-aluminium hydride.

The 3-hydroxy-5β-H steroidal sapogenin initially formed by the said stereospecific reduction may then be converted to a desired derivative form, for example using derivatisation techniques well known in the art. The said conversion may take place in situ or in a different reaction system, and may be simultaneous with the reduction or subsequent to it.

The term "hindered organoborane" as used herein refers particularly to alkali metal tri-alkyl or tri-aryl borohydride reducing agents, such as, for example, lithium tri-sec-butylborohydride, lithium trisiamylborohydride or lithium triphenylborohydride, or the corresponding reducing agents with lithium replaced by potassium or sodium. Alkyl groups preferably contain from 1 to 7 carbon atoms, most preferably from 3 to 7 carbon atoms. Aryl groups preferably contain from 6 to 12 carbon atoms and may be alkyl-substituted. Such reducing agents are sometimes collectively referred to as "Selectride" reducing agents, although it must be understood that as used herein the term "Selectride" is not intended to limit the invention to a reducing agent obtained from any particular manufacturer or source, and such reducing agents from any manufacturer or source can be used. For a more detailed discussion, refer to "Reductions by the Alumino-and Borohydrides in Organic Synthesis", by J. Seyden-Penne (VCH Publishers, Inc.). Preferred hindered organoboranes for use in the present invention are lithium tri-sec-butylborohydride (L-Selectride), potassium tri-sec-butylborohydride (K-Selectride), sodium tri-sec-butylborohydride (N-Selectride), lithium trisiamylborohydride (LS-Selectride), potassium trisiamylborohydride (KS-Selectride), potassium triphenylborohydride and lithium triphenylborohydride.

The term "organo-aluminium hydride" as used herein refers particularly to any reducing agent containing aluminium and hydride moieties and organic groups (e.g. alkyl or alkoxy, suitably containing from 1 to 7 carbon atoms), such as sodium bis-(2-methoxyethoxy)aluminium hydride (Red-Al®), diisobutyl-aluminium hydride (DIBAL) or lithium tri-tert-butoxyaluminohydride (LTBA). For more detailed discussion, refer to "Reductions by the Alumino- and Borohydrides in Organic Synthesis", by J. Seyden-Penne (VCH Publishers, Inc.). Preferred organo-aluminium hydrides for use in the present invention are Red-Al, DIBAL and LTBA.

The term "derivative" used herein in relation to sapogenins refers particularly to the corresponding saponins and other physiologically acceptable forms such as salts and esters, which may serve as pro-drugs. Sapogenins and their derivatives may readily be interconverted by reactions which are well known in the art. Derivative forms of sapogenins may carry derivatised groups at any desired one or more positions of the molecule. Saponin and ester derivatives may, for example, carry derivatised groups at the 3-position in the A ring. The expression "sapogenin" used herein shall be taken to include all derivative forms thereof, unless the contrary is apparent from the context.

In connection with the third aspect of the present invention, discussed below, the term "derivative" used herein refers additionally to activated derivatives of sapogenins, usable in that reaction.

By appropriate selection of the reducing agent, the method enables a range of 3α-hydroxy, 5β-H and 3β-hydroxy,5β-H sapogenins and their derivatives to be prepared in substantially or at least predominantly stereoisomerically pure form in good or excellent overall yield (e.g. above about 80% conversion) from a commercially available or readily prepared starting material, generally with avoidance of difficult separation of isomer mixtures.

The use of the hindered organoborane or organo-alumino hydride reducing agents has not been applied previously to 3-keto-5β-H steroidal sapogenins. Miles's preparation (*J. Agric. Food Chem.*, 41, 914-917 (1993)) of episarsasapogenin, the disclosure of which is incorporated herein by reference, utilised sodium borohydride as the reducing reagent, even though the more selective reagent LTBA was known at the time this work was reported.

Where the reducing agent is a relatively highly hindered organoborane (organic groups more than about two carbon atoms), the sapogenin obtained may predominantly be a 3β-hydroxy,5β-H sapogenin.

Where the reducing agent is a relatively less hindered organoborane (organic groups up to about two carbon atoms), the sapogenin obtained may predominantly be a 3α-hydroxy, 5β-H sapogenin.

Where the reducing agent is an organo-aluminium hydride, the sapogenin obtained may predominantly be a 3α-hydroxy, 5β-H sapogenin.

The expression 3-keto,5β-H sapogenin is used herein for convenience, to refer to the starting material for the reduction, and does not necessarily imply saturation or the absence of keto groups at other parts of the molecule, e.g. outside the A ring, provided that, if necessary, any undesirably reactive sites at other parts of the molecule are suitably protected. The 3-keto,5β-H sapogenin starting material can be different from the desired end product in parts of the molecule other than the 3 position in the A ring; in this case, the necessary conversion(s) will be performed in a manner known to those skilled in this art, as part of the overall synthetic route leading to the desired end product.

The 3-keto,5β-H steroidal sapogenin starting material may suitably be prepared by oxidation of the corresponding 3-OH sapogenin. For example, sarsasapogenone has been prepared by oxidation with pyridinium dichromate as described by Miles (*J. Agric Food Chem.*, 41, 914-917 (1993)), Jones oxidation as described by Blunden (*J. Nat. Prod.*, 42, 478-482 (1979)) and in WO-98/07741, the disclosures of which are incorporated herein by reference. Smilagenone has been produced from diosgenone (itself prepared by the oxidation of diosgenin) utilizing the reduction of the double bond of the α,β unsaturated ketone [Marker et al., *J. Am. Chem. Soc.* 2525 (1940), Irismetov & Goryaev, *Izv. Akad. Nauk Kaz. SSR, Ser. Khim.*, 2, 47-52 (1981)].

In a preferred embodiment of the present invention, the 3-keto, 5β-H steroidal sapogenin starting material is prepared by heterogeneous catalytic hydrogenation of a corresponding $\Delta^4$,3-keto steroidal sapogenin, for example diosgenone. The heterogeneous catalytic hydrogenation converts the $\Delta^4$, 3-keto steroidal sapogenin predominantly to the corresponding 5β-H 3-ketone product, for example smilagenone, which is then reduced in accordance with the first aspect of the present invention.

The heterogeneous catalytic hydrogenation may suitably be performed using hydrogen and a palladium catalyst in an organic solvent. The palladium catalyst is preferably present on a support such as, for example, barium sulphate, calcium carbonate, graphite or carbon. The palladium is preferably used in a pre-reduced form.

Where diosgenone is the starting material and the catalytic hydrogenation is followed by reduction of the smilagenone using a hindered organoborane reducing agent, the product obtained is smilagenin.

Where diosgenone is the starting material and the catalytic hydrogenation is followed by reduction of the smilagenone using an organo-alumino hydride reducing agent, the product obtained is epismilagenin.

The present invention provides in a second aspect a method for the conversion of 3α-hydroxy-5β-H steroidal sapogenins and derivatives thereof to 3β-hydroxy-5β-H steroidal sapogenins and derivatives thereof, which comprises contacting a 3-hydroxy activated derivative of a 3α-hydroxy-5β-H steroidal sapogenin with a nucleophile under conditions favouring nucleophilic substitution with inversion at the 3-position, with optional subsequent adjustment of the 3-substituent as desired.

The reaction will proceed via an $S_N2$ mechanism, to lead to the required inversion product. One reaction protocol which may particularly be mentioned is the Mitsonobu reaction (Hughes, *Organic Reactions*, 42, 337-400 (1992)). When such a protocol is applied to a sapogenin, a 3-OH sapogenin is converted, via a 3-hydroxy activated form thereof, to a corresponding 3-ester with inversion at the 3-position. The reagents used are a dialkylazodicarboxylate, a triarylphosphine and the appropriate organic acid or salt thereof according to the desired ester. The term "alkyl" preferably refers to alkyl groups containing from 1 to 7 carbon atoms. The term "aryl" preferably refers to aryl groups containing from 6 to 12 carbon atoms and such aryl groups may optionally be alkyl-substituted.

An alternative reaction protocol may involve the initial preparation of an activated derivative of the sapogenin which is capable of participating in the nucleophilic substitution, such as for example an organic sulphonated derivative at the 3-O position, such as a 3-mesylate or 3-tosylate derivative.

Where the organic acid used in the said reaction according to the second aspect of the present invention includes a group such as an amino group which would otherwise participate undesirably in the reaction, such a group will suitably be protected in conventional manner.

Viewed overall, the present invention provides a procedure for the synthesis of useful steroidal sapogenins, e.g. smilagenin or epismilagenin, from readily available materials, e.g. diosgenin, utilising selective reductions to control stereochemistry, as represented for these specific compounds in Scheme 1 below:

The methods of the present invention can be used for the preparation of a 3-hydroxy 5β-H steroidal sapogenin, such as sarsasapogenin, smilagenin, episarsasapogenin and epismilagenin and derivatives thereof. Pro-drugs and other physiologically acceptable forms of the sapogenins may be prepared from the 3-OH compounds in conventional manner, as described in more detail below.

DETAILED DESCRIPTION OF THE INVENTION

The Sapogenin End Products

The method of the present invention is preferably used to prepare sapogenin end products selected from compounds of general formula:

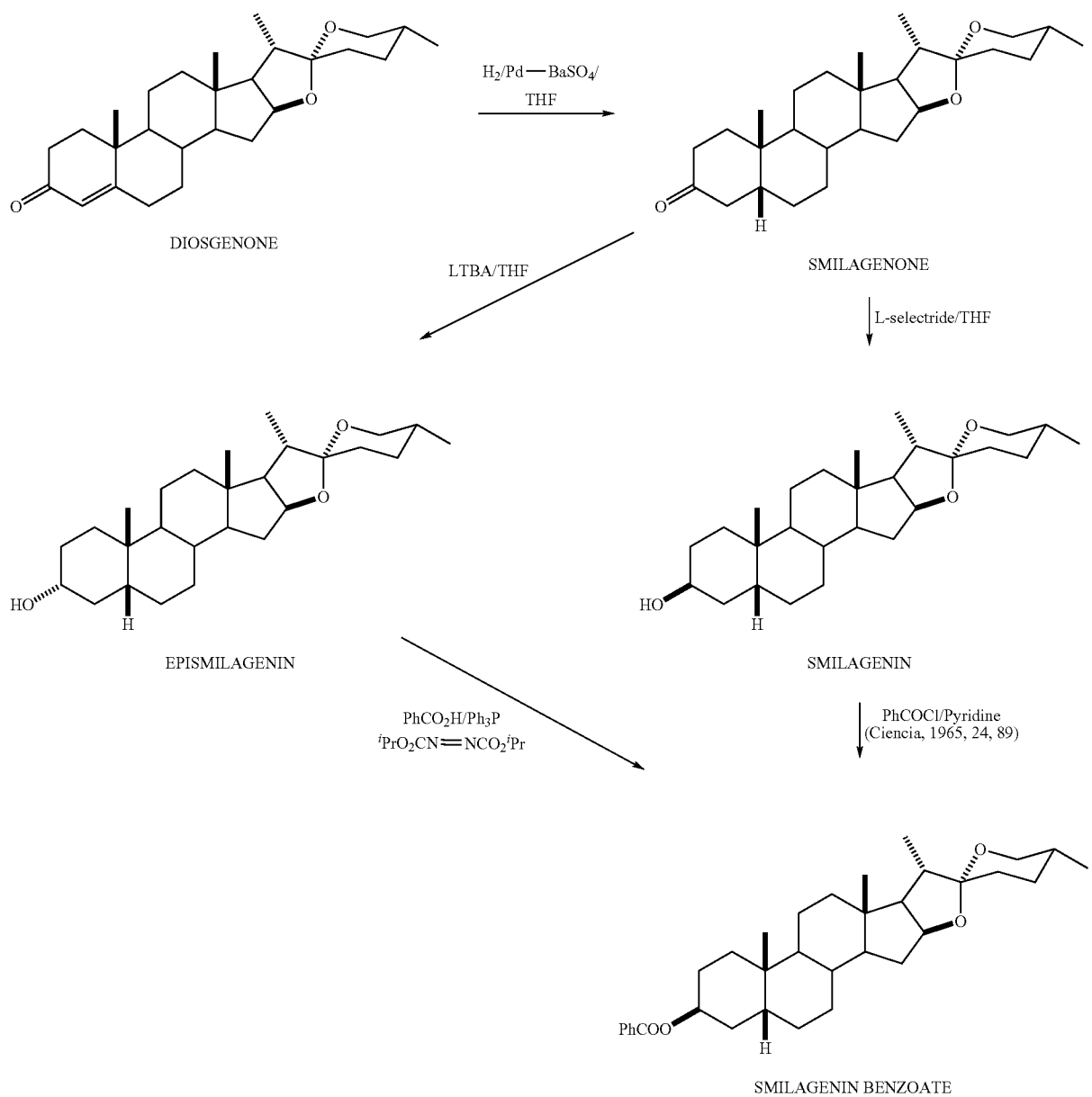

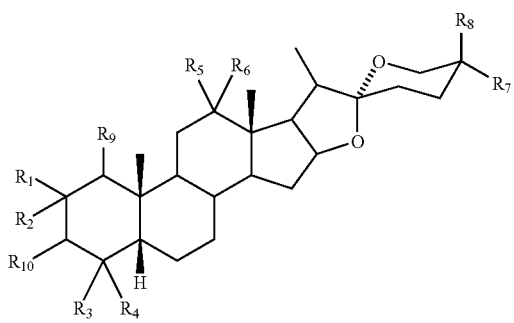

wherein $R_1$, $R_2$, $R_3$, $R_4$, $R_5$, $R_6$, $R_7$, $R_8$ and $R_9$ are, independently of each other, H, $C_{1-4}$ alkyl, OH, or OR (where R= $C_{6-12}$ aryl or $C_{1-4}$ alkyl), or $R_5$ and $R_6$ together may represent a =O (carbonyl) or protected carbonyl group, the stereochemistry at carbon centre 3 (i.e the A ring carbon to which the group $R_{10}$ is attached) can be either R or S, and $R_{10}$ can be OH, an O-linked sugar group or any organic ester group (which includes aliphatic and amino acid esters).

Except where specified in the above formula using the wedge and dash convention, and except as far as stereospecificity is a feature of the invention, the stereochemistry in the formula is unspecified and all stereoisomers and isomer mixtures are included.

The term "Physiologically acceptable prodrug" as used herein means those prodrugs of the compounds useful according to the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. A thorough discussion of prodrugs is provided in the following: Design of Prodrugs, H. Bundgaard, Ed., Elsevier, 1985; Methods in Enzymology, K. Widder et al, Ed., Academic Press, 42, p. 309-396, 1985; A Textbook of Drug Design and Development, Krogsgaard-Larsen and H. Bundgaard, Ed., Chapter 5; Design and Applications of Prodrugs, p. 113-193, 1991; Advanced Drug Delivery Reviews, H. Bundgaard, 8, p. 1-38 (1992); Journal of Pharmaceutical Sciences, 77, p. 285 (1988); Chem. Pharm. Bull., N. Nakeya et al, 32, p. 692 (1984); Pro-drugs as Novel Delivery Systems, T. Higuchi and V. Stella, Vol. 14 of the A.C.S. Symposium Series, and Bioreversible Carriers in Drug Design, Edward B. Roche, Ed., American Pharmaceutical Association and Pergamon Press, 1978, which are incorporated herein by reference.

The term "physiologically acceptable salts" means the relatively non-toxic, inorganic and organic acid addition salts, and base addition salts, of compounds of the present invention. These salts can be prepared in situ during the final isolation and purification of the compounds or by separately reacting the purified compound. See, for example, S. M. Berge et al, Pharmaceutical Salts, J. Pharm. Sci., 66: p. 1-19 (1977), which is incorporated herein by reference.

The term "organic ester" as used herein refers to any ester formable by reaction of the compound in which $R_{10}$ is OH with an ester-forming organic acid or activated derivative thereof. The organic acid may, for example, be an aliphatic carboxylic acid or an amino acid. Without limitation, the organic ester group may, for example, be selected from: cathylate (ethoxycarbonyloxy), acetate, succinate, propionate, n-butyrate, i-butyrate, valerate, isovalerate, n-caproate, iso-caproate, diethylacetate, octanoate, decanoate, laurate, myristate, palmitate, stearate, benzoate, phenylacetate, phenylpropionate, cinnamate, phthalyl, glycinate, alaninate, valinate, phenylalaninate, isoleucinate, methioninate, argininate, aspartate, cysteinate, glutaminate, histidinate, lysinate, prolinate, serinate, threoninate, tryptophanate, tyrosinate, fumerate, maleate, substituted aliphatic, e.g. chloroacetate, methoxyacetate, protected amino acid ester groups, e.g. Boc-aminoglycinate (Boc=t-butoxycarbonyl), Boc-aminovalinate, CBZ-aminoglycinate (CBZ=benzyloxycarbonyl), CBZ-aminoalinate, and substituted aromatic ester groups, e.g. p-bromobenzoyloxy, m-bromobenzoyloxy, p-methoxybenzoyloxy, chlorobenzoate such as p-chlorobenzoyloxy, dichlorobenzoate such as 2,4-dichlorobenzoyloxy, nitrobenzoate such as p-nitrobenzoyloxy or 3,5-dinitrobenzoyloxy, etc.

The term "sugar" as used herein refers particularly to a mono-, di-or tri-saccharide, and acylated forms thereof. Without limitation, such a sugar may, for example be a mono aldose or ketose having 5 or 6 carbon atoms, preferably in the cyclised furanose or pyranose form, either as the α or β anomer and having D or L optical isomerism. Examples of suitable sugars include glucose, mannose, fructose, galactose, maltose, cellobiose, sucrose, rhamnose, xylose, arabinose, fucose, quinovose, apiose, lactose, galactose-glucose, glucose-arabinose, fucose-glucose, rhamnose-glucose, glucose-glucose-glucose, glucose-rhamnose, mannose-glucose, glucose-(rhamnose)-glucose, glucose-(rhamnose)-rhamnose, glucose-(glucose)-glucose, galactose-(rhamnose)-galactose and acylated (e.g. acetylated) derivatives thereof.

The First Aspect of the Invention

The 3-keto,5β-H steroidal sapogenin, the starting material for the step which results in the preparation of the desired sapogenin according to the first aspect of the present invention, preferably corresponds to the desired sapogenin at all points of the molecule except the 3-position group. However, if necessary or desirable, suitable protective groups may be applied for the reduction, and subsequently removed to yield the desired sapogenin.

The term "protective groups" used herein refers to groups which are used to protect reactive functional groups, for example hydroxy or carboxy groups, where these are desired in the final product, to avoid their unwanted participation in the reactions. Conventional protecting groups may be used in accordance with standard practice, for examples see T. W. Green and P. G. M. Wuts in "Protective Groups in Organic Chemistry" John Wiley and Sons, 1991; J. F. W McOmie in "Protective Groups in Organic Chemistry" Plenum Press, 1973.

A number of reagents have been discovered to effect selectivity to either afford smilagenin or epismilagenin, as shown in Table 1 below (selectivity percentages refer to components in the crude product). Surprisingly we have found that the use of K-, L-or N-Selectride® (potassium, lithium or sodium tri-sec-butylborohydride) or the corresponding triphenylborohydride leads to the formation of the 3β-hydroxyl, e.g. smilagenin, in a highly stereoselective manner. The use of the less hindered lithium triethylborohydride reducing agent leads to the formation of the 3α-hydroxyl, e.g. epismilagenin, in a highly stereoselective manner. Surprisingly, we have also found that the use of an organo-aluminium hydride such as LTBA also leads to the formation of the 3α-hydroxyl, e.g. epismilagenin, in a highly stereoselective manner.

In the stereoselective reduction of 3-keto,5β-H steroidal sapogenins according to the present invention, we have found that it is possible to obtain in the end product a molar ratio of the predominant 3-hydroxy steroid obtained to the alternative 3-epimer, of at least about 10:1, with examples of at least about 15:1.

TABLE 1

Selectivity in the reduction of smilagenone.

| Reagent | Temp/° C. | Solvent | Smilagenin/% | Epismilagenin/% | Smilagenone/% |
|---|---|---|---|---|---|
| LiAlH(O$^t$Bu)$_3$ | RT | THF | 5.0 | 95.0 | — |
| LiBHEt$_3$ | −78 | THF | 22.8 | 74.3 | — |
| *AlH$_3$ | 0 | THF | 14.4 | 83.1 | — |
| *BH$_3$ | 0 | THF | 11.8 | 83.9 | — |
| *9-BBN | −78 | THF | 10.4 | 51.4 | 37.5 |
| *NaBH$_4$/CeCl$_3$ | −78 | THF | 4.4 | 89.5 | — |
| L-selectride ® | −78 | THF | 91.1 | 3.4 | 4.7 |
| L-selectride ® | −5 | THF | 92.7 | 4.2 | 2.5 |
| L-selectride ® | 20 | THF | 92.7 | 4.8 | 2.2 |
| L-selectride ® | −78 | Toluene | 90.8 | 5.5 | 2.5 |
| L-selectride ® | −78 | DEM | 54.0 | 4.0 | 41.1 |
| L-selectride ® | 20 | Cyclohexane | 74.9 | 13.9 | 8.5 |
| N-selectride ® | −78 | THF | 97.3 | 1.6 | 0.2 |
| N-selectride ® | −5 | THF | 94.2 | 2.6 | 0.5 |
| K-selectride ® | −78 | THF | 96.5 | 2.0 | 0.3 |
| K-selectride ® | −10 | THF | 93.6 | 4.0 | 0.6 |
| K-selectride ® | −78 | MTHF | 92.2 | 6.3 | — |
| LS-selectride ® | −78 | THF | 91.5 | 4.4 | 3.2 |
| KS-selectride ® | −78 | THF | 95.5 | 2.4 | 0.3 |
| KBH(Ph)$_3$ | −78 | THF | 91.0 | 4.6 | 1.7 |

*= comparison reactions

We have found, surprisingly, that low temperatures (e.g. around −78° C.) are not essential to the method of the present invention. The reduction may generally be carried out at a temperature from −100° C. to 25° C., preferably from −40° C. to 25° C., most preferably at about −10° C. to 10° C., and suitably in a solvent selected from tetrahydrofuran (THF), 2-methyltetrahydrofuran (MTHF), toluene, 1,4-dioxane, tert-butyl methyl ether, and mixtures of these solvents, most preferably THF.

In a preferred embodiment, the 3-keto,5β-H steroidal sapogenin starting material, for example smilagenone, is prepared by heterogeneous catalytic hydrogenation of a corresponding $\Delta^4$,3-keto steroidal sapogenin, for example diosgenone.

This $\Delta^4$, 3-keto steroidal sapogenin, for example diosgenone, is itself preferably prepared by an oxidation of the corresponding $\Delta^5$, 3-hydroxy steroidal sapogenin, for example diosgenin, to afford the αβ-unsaturated ketone. It will be noted that the direct reduction of diosgenin using palladium on carbon as a catalyst gives predominantly the 5α-product, tigogenin.

Marker (Marker et al, *J. Am. Chem. Soc.*, 62, 2525 (1940)) has shown that the reduction of diosgenone to smilagenone can be achieved with palladium-barium sulphate catalyst in ether solution under hydrogen. The low concentration (500 volumes; normal processing volumes are in the range of 5-30 volumes) and high catalyst loading (1000%; normal catalyst loadings are in the range 1-20%) render the process as described unfeasible and uneconomical for large-scale work. An additional consideration is that ether is unsuitable for large-scale work for safety reasons.

Other workers have also investigated the reduction of diosgenone to smilagenone. Djerassi reduced diosgenone (10 g) in ethanol (450 ml) over pre-reduced 10% Pd-C (0.8 g) at atmospheric pressure. Crude smilagenone was isolated by precipitation with water and recrystallised from chloroform/methanol to furnish pure smilagenone (7.2 g, 72%) with a melting point of 179-183° C. The yield was not changed when the reaction was carried out in the presence of potassium hydroxide (3 g). An analytically pure sample melted at 186-188° C. (Djerassi, Yashin and Rosenkranz, *J. Am. Chem. Soc.*, 74, 422 (1952)). This process suffers from low dilution due to the low solubility of diosgenone in ethanol.

In the pregnane series Suvorov has found that pyridine has a marked effect upon the outcome of such hydrogenation reactions. Typically, in this work the catalyst of choice was 10% palladium on calcium carbonate (Pd—CaCO$_3$). In such cases the selectivity was found to be markedly superior to those reactions run in alcoholic solvents, even with the addition of caustic (Suvorov and Yaroslavtseva, *Steroids*, 1270 (1961)). The work-up employed in this study involved quenching onto dilute hydrochloric acid and extraction of the product into chloroform. The organic extract was washed with dilute hydrochloric acid, 8% aqueous sodium bicarbonate solution and water until neutral to litmus. Such methods lead to the production of large amounts of aqueous waste containing pyridine and halogenated solvents that require disposal, adding to the cost of processing.

Irismetov demonstrated that high selectivity could be achieved in the reduction of diosgenone to smilagenone. In this work diosgenone (1 g) was hydrogenated over 5% Pd—CaCO$_3$ (1 g) in pyridine (30 ml) at atmospheric pressure. After filtration to remove the catalyst and solvent evaporation the residue was crystallised from alcohol to afford a solid melting at 209-211° C. No yield is given (Irismetov and Goryayev, *Izv. Akad. Nauk Kaz. SSR, Ser. Khim.*, 2, 47 (1982)). For large-scale production this work suffers from high catalyst loadings (100%) and dilute solutions. Pyridine is a noxious solvent and is more generally used in stoichiometric amounts as an acid scavenger in large-scale work.

British patent No. 736,818 makes a claim for the reduction of 3-keto-$\Delta^4$-steroids to 5β-H steroids with a palladium catalyst, in the presence of an inorganic base and in an anhydrous medium. The preferred solvent is methanol and the preferred base is potassium hydroxide. Diosgenone is not exemplified. We find that diosgenone is poorly soluble in alcohols (specifically ethanol), which would render this process very dilute. Such a method also requires an extractive work-up procedure.

British patent No. 763,301 makes a reference to the utility of alkali (i.e. sodium or potassium hydroxide) in increasing the amount of 5β-H product in the reduction of 3-keto-$\Delta^4$-steroids. This patent makes a specific claim for the utility of triethylamine in this context. Of the solvents chosen ethanol, ether, ethyl acetate and methylcyclohexane are cited, with 1,4-dioxane being the preferred solvent.

We have made the surprising discovery that the use of palladium on a support such as barium sulphate (Pd—$BaSO_4$) or calcium carbonate (Pd—$CaCO_3$) in a suitable solvent provides an economic and scaleable process. Specifically we have discovered processes that operate at commercially viable concentrations using low catalyst loadings. Furthermore we have surprisingly found that the reduced forms of these catalysts are more selective than the unreduced forms as shown in Table 2 below.

Increased temperature was also found to diminish the selectivity. The reaction is preferably operated at 15-75° C., preferably at 20-50° C. and most preferably at 20-30° C.

THF offered an improved solubility of diosgenone when compared to ethanol and other possible ether-replacement solvents such as diethoxymethane and tert-butyl methyl ether. This provides a higher throughput and more economic process. This process provided a simple work-up when compared to the ethanol/aqueous sodium hydroxide system.

The work-up consisted of concentration of the reaction mixture and isolation of the smilagenone. The solvent may be optionally recycled.

A number of solvents were effective in achieving purification of the smilagenone, including cyclohexane, 2-butanone, acetone, 2-propanol and methanol; examples of these are shown in Table 3 below.

TABLE 2

General screening studies

| Solvent/Catalyst | Smilagenone/% | Tigogenone/% | Diosgenone/% | Tigogenin/% |
|---|---|---|---|---|
| Pd—$BaSO_4$ (r)/THF/ | 95.7 | 2.1 | <0.1 | 1.2 |
| Pd—$BaSO_4$ (u)/THF | 84.0 | 13.1 | — | — |
| Pd—$CaCO_3$ (r)/THF | 91.4 | 6.9 | — | 1.7 |
| Pd—$CaCO_3$ (u)/THF | 81.1 | 14.2 | — | 1.7 |

Note:
(r) indicates the reduced form of the catalyst and (u) the unreduced form.

5% Pd/graphite (Johnson Matthey type 450) and 10% Pd/C (Johnson Matthey type 39) are also suitable catalysts for the process.

Suitable solvents may be selected from tetrahydrofuran (THF), 2-methyltetrahydrofuran, toluene, 1,4-dioxan, ethyl acetate, methyl iso-butylketone, most preferably THF. These solvents are found to be advantageous over pyridine. With these solvents, the process can be operated at a concentration of 1 volume to 50 volumes, preferably 3-30 volumes and most preferably at 3-10 volumes. The catalyst loading is in the range of 1 to 25%, preferably 1 to 10% and most preferably 1-5%.

Surprisingly we have discovered that an increase in pressure resulted in a lower selectivity for the process. The reaction is preferably operated at 1-5 bar hydrogen and most preferably at 1-2 bar hydrogen.

TABLE 3

Recrystallisation of crude smilagenone

| Solvent | Volumes | Yield/% | Smilagenone % | Tigogenone % | Diosgenone % | Tigogenin % |
|---|---|---|---|---|---|---|
| Input | — | — | 91.35 | 5.15 | 1.71 | 1.27 |
| 2-Butanone | 5 | 70 | 97.77 | 1.20 | 0.39 | 0.51 |
| Cyclohexane | 8 | 72 | 97.71 | 1.10 | 0.33 | 0.57 |
| 2-Propanol | 12 | 60 | 97.40 | 1.35 | 0.37 | 0.71 |

A preferred aspect of the invention is to take a solution of smilagenone in THF from the hydrogenation directly into the reduction according to the first aspect of the present invention. This avoids the need for work-up, isolation and drying of the intermediate smilagenone, providing savings in time and equipment usage and therefore expected improvements in manufacturing costs. We have surprisingly found that the impurities generated by this process (mainly epitigogenin and epismilagenin) can be removed by recrystallisation of the crude smilagenin.

The Second Aspect of the Invention

In the second aspect of the invention, there is provided the conversion of 3α-hydroxy-5β-H steroidal sapogenins and derivatives thereof to 3β-hydroxy-5β-H steroidal sapogenins and derivatives, e.g. esters, thereof, by a stereospecific inversion reaction. For example, episarsasapogenin can be smoothly converted to the novel compound sarsasapogenin benzoate by the action of diisopropylazodicarboxylate, triphenylphosphine and benzoic acid, the so-called Mitsonobu reaction (Hughes, *Organic Reactions*, 42, 337-400 (1992)). Sarsasapogenin benzoate and its preparation therefore constitute further features of the present invention. In a similar fashion, epismilagenin can be converted to the known ester smilagenin benzoate. The process is not restricted to benzoate esters but may usefully be employed to make aliphatic, eg, acetate, propionate, n-butyrate, i-butyrate, n-caproate, i-caproate, palmitate, substituted aliphatic, e.g. chloroacetate, methoxyacetate, protected amino esters, eg Boc-aminoglycinate, Boc-aminovalinate, CBZ-aminoglycinate, CBZ-aminoalinate, or substituted aromatic esters, eg chlorobenzoate, nitrobenzoate, dichlorobenzoate etc.

The reaction protocol may alternatively include preliminary formation of an activated form of the 3α,5β-sapogenin such as the methanesulphonate (mesylate) or p-toluenesulphonate (tosylate). This activated form can then be reacted with an anionic salt of the carboxylic acid (e.g. the sodium, caesium or potassium salt), in conventional manner for nucleophilic substitution.

Recovery of the Obtained Compound

The compound prepared according to either aspect of the present invention may be recovered from the reaction mixture by conventional means. For example, the compounds may be recovered by distilling off the solvent from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well known techniques, such as recrystallization, re-precipitation or the various chromatography techniques, notably column chromatography or preparative thin layer chromatography.

EXAMPLES

The following Examples illustrate, without limitation, the synthesis of episarsasapogenin, smilagenin, and epismilagenin utilising selective reductions to control stereochemistry. The Examples also illustrate the stereospecific conversion of 3α-hydroxy,5β-H sapogenins to 3β-hydroxy,5β-H sapogenins and derivatives thereof.

Example 1

Synthesis of Smilagenin from Smilagenone with L-Selectride® at −10° C.

Smilagenone (657 g) was dissolved in tetrahydrofuran (4000 ml) and the solution purged with nitrogen and cooled to provide an internal temperature of ca. −10° C. L-Selectride® (2400 ml 1M in THF) was added over ca. 50 minutes and stirred for 90 minutes. A solution of citric acid (600 g) in water (2000 ml) was added slowly, maintaining the temperature below 0° C. The mixture was allowed to warm to ambient temperature and stirred for 30 minutes. The aqueous layer was separated and extracted with dichloromethane (2000 ml) and the layers separated. The aqueous layer was extracted with dichloromethane (1500 ml). The combined organic extracts were washed with water (4000 ml) and dried over $MgSO_4$. The organic extracts were evaporated to dryness to yield smilagenin.

Example 2

Synthesis of Smilagenin from Smilagenone with K-Selectride® at −15° C.

K-Selectride® (1600 ml; 1M in THF) was added to a solution of smilagenone (500 g) in THF (3500 ml) at ca. −15° C. under an atmosphere of nitrogen. The reaction mixture was stirred at this temperature for 30 minutes and quenched with aqueous citric acid (393 g in 1300 ml water), maintaining the internal temperature at ca. 0° C. The mixture was warmed to ambient temperature and the THF evaporated at atmospheric pressure until a solid precipitated. The solid was filtered off and dried at the pump.

The solid was dissolved in dichloromethane (DCM) (6000 ml), dried ($MgSO_4$) and evaporated to a white solid, which was recrystallised from isopropyl alcohol (IPA) (5000 ml) to afford smilagenin.

Example 3

Synthesis of Smilagenin from Smilagenone with N-Selectride® at −78° C.

N-Selectride® (0.64 ml, 1M in THF) was added to a solution of smilagenone (206 mg) in THF (10 ml) over 10 minutes at −78° C. The mixture was stirred and quenched with 10% aqueous citric acid (2 g in 20 ml water) and the product extracted into DCM (2×50 ml), dried (MgSO4) and evaporated to a colourless oil. The oil was taken up in acetone (20 ml) and water (50 ml) added. The precipitate was collected by filtration and dried to afford smilagenin (200 mg, 97%).

Example 4

Synthesis of Smilagenone from Diosgenone

Diosgenone (500 g) was dissolved in tetrahydrofuran (THF) (2500 ml) at 40-45° C. and inerted with nitrogen. 5% Pd—$BaSO_4$ (reduced) (100 g) was added; the flask was purged with hydrogen and stirred under an atmosphere of hydrogen for ca. 6.5 hours. The flask was cooled to ambient temperature and the catalyst removed by filtration through a pad of Celite (50 g). The solvent evaporated to yield crude smilagenone as a solid residue.

This process was repeated and the two batches combined (902.8 g) and reslurried in cyclohexane (2260 ml) at ambient temperature under a nitrogen atmosphere for ca. 30 minutes. The solid was harvested by filtration and dried in a vacuum oven at ca. 40° C. overnight to yield purified smilagenone (749.1 g; 75%).

Example 5

Synthesis of Smilagenone from Diosgenone

Diosgenone (700 g) was dissolved in tetrahydrofuran (THF) (4500 ml) and inerted with nitrogen. The mixture was treated with activated carbon (35 g) and hydrogenated over 5% Pd—$BaSO_4$ (reduced) (35 g) at 25° C. and 2.5 barg hydrogen. The catalyst was removed by filtration and the mixture concentrated to ca. quarter volume. Water (3000 ml) was added over ca. 30 minutes and the resultant solid filtered. The solid was washed with methanol (560 ml) and dried under vacuum at 40-50° C. to afford smilagenone (630 g, 90%).

Example 6

Telescoping of the Hydrogenation and Reduction Reactions

Diosgenone (500 g) was dissolved in tetrahydrofuran (2500 ml) and inerted with nitrogen. 5% Pd—BaSO$_4$ (reduced) (100 g) was added; the flask was purged with hydrogen and stirred under an atmosphere of hydrogen for ca. 5 hours. The catalyst was removed by filtration through a pad of Celite (20 g). The residue was washed with tetrahydrofuran (1000 ml) and the solution used directly in the next stage.

K-Selectride® (1600 ml; 1M in tetrahydrofuran) was added to the solution of smilagenone (500 g) in tetrahydrofuran from above at ca. −15° C. under an atmosphere of nitrogen. The reaction mixture was stirred at this temperature for 30 minutes and quenched with aqueous citric acid (393 g in 1300 ml water), maintaining the internal temperature at ca. 0° C. The mixture was warmed to ambient temperature and the tetrahydrofuran evaporated at atmospheric pressure until a solid precipitated. The solid was filtered off and dried at the pump.

The solid was dissolved in dichloromethane (6000 ml), dried (MgSO$_4$) and evaporated to a white solid, which was recrystallised from 2-propanol (5000 ml). The solid was further recrystallised from acetone (5000 ml). The solid was further recrystallised from acetone (3500 ml). The solid was dried at 80° C. in a vacuum oven to afford pure smilagenin (154.5 g).

mp 184.7-187.0° C.; $[\alpha]_D^{20}$=−73.3°; IR $v_{max}$ 3456, 2928, 1451, 1376, 1050, 979, 896 cm$^{-1}$; ESI-MS m/z 417 [M+1]$^+$; $^1$H NMR (CDCl$_3$, 300 MHz): inter alia δ 4.39 (1H, br q, J=8 Hz), 4.10 (1H, br s), 3.46 (1H, br dd, J=11 Hz), 3.39 (1H, t, J=11 Hz), 0.98 (3H, s), 0.97 (3H, d, J=7 Hz), 0.79 (3H, d, J=7 Hz), 0.76 (3H, s) ppm; $^{13}$C NMR (CDCl$_3$, 126 MHz): δ 14.47, 16.43, 17.10, 20.83, 23.86, 26.48, 26.50, 27.75, 28.73, 29.89, 30.24, 31.32, 31.73, 33.46, 35.21, 35.21, 36.45, 39.78, 40.24, 40.63, 41.54, 56.41, 62.19, 66.79, 66.98, 80.87, 109.20 ppm; C 77.94%; H 10.75% (theoretical value for C$_{27}$H$_{44}$O$_3$: C 77.84%; H 10.64%).

Example 7

Telescoping of the Hydrogenation and Reduction Reactions

L-Selectride® (527 ml; 1M in tetrahydrofuran) was added to a solution of smilagenone (156 g) in tetrahydrofuran (obtained by hydrogenation of diosgenone) at ca. −10° C. under an atmosphere of nitrogen. The reaction mixture was stirred at this temperature for 30 minutes, allowed to warm to ambient temperature and stirred overnight. The mixture was quenched by addition to a mixture of aqueous citric acid (311 g in 3800 ml water) and dichloromethane (2200 ml), maintaining the internal temperature below 30° C. The aqueous phase was separated and re-extracted with dichloromethane (400 ml). The combined organic extracts were washed with aqueous citric acid (160 g in 2200 ml water) and distilled to low volume. 2-Propanol (3000 ml) was added and the mixture redistilled to ca. ½ volume. Additional 2-propanol (1500 ml) was added and the mixture distilled to ca. ½ volume. The mixture was heated to reflux and allowed to cool. The mixture was further cooled to 0-10° C. and filtered. The solid was dried in a vacuum oven at 60-65° C. to afford smilagenin. The yield is 94.0 g.

Example 8

Reduction of Smilagenone to Epismilagenin

Lithium tri-tert-butoxyaluminohydride (1M in tetrahydrofuran, 99 ml) was added dropwise to a solution of smilagenone (32.0 g, 77.2 mmol) in tetrahydrofuran (800 ml) at such a rate that a temperature of 14-16° C. was maintained. Once addition was complete the mixture was stirred at room temperature for a further 2 hr. The remaining reducing agent was quenched by the careful addition of ammonium chloride solution (30 g in 400 ml water). The mixture was filtered and the solid washed with dichloromethane (300 ml). The combined filtrates were evaporated and the residue partitioned between dichloromethane (300 ml) and water (300 ml). The aqueous layer was further extracted with dichloromethane (2×300 ml). The combined organics were dried (MgSO$_4$) and evaporated to afford a white solid (25.7 g). The solid was recrystallised from acetone (1250 ml) and the resultant solid (19.0 g) dried in a vacuum oven at 40° C. overnight. The solid was further purified by heating a suspension in acetone (1425 ml). The resultant solid was dried in a vacuum oven at 40° C. overnight. The solid was finally purified by recrystallisation from 2-propanol (300 ml) and the solution hot-filtered to remove any inorganics. The filtrate was cooled, the solid filtered and dried at 60° C. in a vacuum oven overnight to afford epismilagenin (9.0 g).

mp 223-227° C.; $[\alpha]_D^{25}$=−64° (c=5 g l$^{-1}$, CHCl$_3$); IR $v_{max}$(KBr) 3392, 2937, 1451, 1369, 1051, 982, 864 cm$^{-1}$; ESI-MS m/z 417 [M+1]$^+$; $^1$H NMR (CDCl$_3$, 300 MHz): inter alia δ 4.40 (1H, br q, J=8 Hz), 3.62 (1H, septet, J=10, 10, 5, 5 Hz), 3.48 (1H, br dd, J=11 Hz), 3.37 (1H, t, J=11 Hz), 0.97 (3H, d, J=7 Hz), 0.95 (3H, s), 0.79 (3H, d, J=7 Hz), 0.75 (3H, s) ppm; $^{13}$C NMR (CDCl$_3$, 75 MHz) inter alia: δ 14.91, 16.85, 17.55, 20.99, 23.78, 27.08, 27.49, 30.68, 31.75, 32.18, 35.09, 35.75, 35.85, 40.62, 40.91, 41.04, 41.99, 42.39, 56.74, 62.59, 67.23, 72.10, 81.30, 109.64 ppm; C 77.77%; H 10.59% (theoretical value for C$_{27}$H$_{44}$O$_3$: C 77.84%; H 10.64%).

Example 9

Synthesis of Smilagenin Benzoate from Epismilagenin

A solution of diisopropylazodicarboxylate (0.81 g, 4.0 mmol) in dry THF (2 ml) was added to a stirred solution of epismilagenin (0.83 g, 2.0 mmol), triphenylphosphine (1.05 g, 4.0 mmol) and benzoic acid (0.49 g, 4.0 mmol) in dry THF (20 ml). The mixture was stirred at room temperature and monitored by TLC. After 2 h all the starting material had been consumed. The solvent was removed in vacuo, the residual syrup dissolved in ether (30 ml) and the solution washed with aqueous saturated sodium hydrogen carbonate (25 ml). The organic layer was dried over MgSO$_4$ and passed down a short silica pad, the pad being washed with ether. The combined washings and filtrate were concentrated in vacuo to afford smilagenin benzoate as a white solid.

Example 10

Synthesis of Sarsasapogenin Benzoate from Episarsasapogenin

A solution of diisopropylazodicarboxylate (0.81 g, 4.0 mmol) in dry THF (2 ml) was added to a stirred solution of episarsasapogenin (0.83 g, 2.0 mmol), triphenylphosphine (1.05 g, 4.0 mmol) and benzoic acid (0.49 g, 4.0 mmol) in dry THF (20 ml). The mixture was stirred at room temperature and monitored by TLC. After 2 h all the starting material had been consumed. The solvent was removed in vacuo, the residual syrup dissolved in ether (30 ml) and the solution washed with aqueous saturated sodium hydrogen carbonate (25 ml). The organic layer was dried over $MgSO_4$ and passed down a short silica pad, the pad being washed with ether. The combined washings and filtrate were concentrated in vacuo to afford sarsasapogenin benzoate as a white solid.

mp 173-175° C.; $^1$H NMR (500 MHz, $CDCl_3$): δ 0.77 (3H, s, 18-$CH_3$), 1.00 (3H, d, J=6.7 Hz, 21-$CH_3$), 1.04 (3H, s, 19-$CH_3$), 1.08 (3H, d, J=7.0 Hz, 27-$CH_3$), 1.1-2.1 (27H, complex multiplet, aliphatics), 3.31 (1H, br. d, J=10.9 Hz, 26-OCHH), 3.96 (1H, br. dd, J=10.9, 2.0 Hz, 26-OCHH), 4.42 (1H, m, 16-OCH), 5.34 (1H, br. s, H-3), 7.44 (2H, br. t, J=7.6 Hz, aromatic H), 7.55 (1H, br. t, J=7.6 Hz, aromatic H), 8.05 (1H, br. d, J=7.6 Hz, aromatic H) ppm; $^{13}$C NMR (125.6 MHz, $CDCl_3$): δ 14.56, 16.28, 16.71, 21.17, 24.28, 25.41, 26.01, 26.19, 26.69, 27.31, 31.02, 31.33, 31.98, 35.37, 35.57, 37.92, 40.28, 40.48, 40.91, 42.36, 56.63 (C-14), 62.33 (C-17), 65.36 (C-26), 71.54 (C-3), 81.22 (C-16), 109.94 (C-22), 128.54 (aromatic C), 129.73 (aromatic C), 131.39 (aromatic C), 132.9 (aromatic C), 166.13 (carbonyl) ppm.

Example 11

Synthesis of Episarsasapogenin from Sarsasapogenone

A solution of lithium tri-tert-butoxyaluminohydride in THF (1M, 41.71 kg) was added (over ca. 2 hours) to a stirred solution of sarsasapogenone (17.38 kg,) in dry THF (ca 70 kg) at −23 to −30° C. under dry nitrogen. The process line was washed with THF and the mixture stirred at −23 to −30° C. for ca. 3 hours. The resulting solution was carefully quenched with aqueous aqueous sodium sulfate solution (5.67 kg in 28.67 kg of water). The inorganic salts were removed by filtration and washed with THF (184 kg). Water (63.18 kg) was added and the bulk of the THF was removed by distillation. Additional water (126.44 kg) was added and the product isolated by filtration. The product was washed with water (2×17.3.8 kg) and acetone (4×13.73 kg). The product was dried at 35-40° C. to afford episarsasapogenin (14.48 kg).

The foregoing broadly describes the present invention without limitation. Variations and modifications as will be readily apparent to those of ordinary skill in this art are intended to be included within the scope of this application and any subsequent patents.

The invention claimed is:

1. A method of stereospecifically preparing a 3β-hydroxy-5β-H steroidal sapogenin of the formula

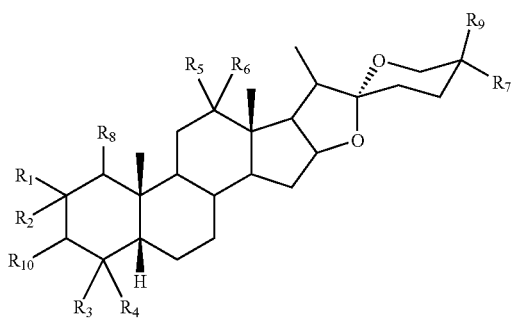

wherein $R_1$, $R_2$, $R_3$, $R_4$, $R_5$, $R_6$, $R_7$, $R_8$ and $R_9$ are, independently of each other, H, $C_{1-4}$ alkyl, OH, or OR (where R= $C_{6-12}$ aryl or $C_{1-4}$ alkyl), or $R_5$ and $R_6$ together may represent a ═O (carbonyl) or protected carbonyl group, the stereochemistry at carbon centre 3 can be either R or S, and $R_{10}$ represents β —OH, which comprises reducing a 3-keto-5β-H steroidal sapogenin using a reducing agent comprising a hindered organoborane.

2. A method according to claim 1, wherein the reducing agent is a hindered organoborane reagent in which organic groups contain more than two carbon atoms and the sapogenin obtained is predominantly a 3β-hydroxy, 5β-H-sapogenin.

3. A method according to claim 1, wherein hindered organoborane is selected from lithium tri-sec-butylborohydride, potassium tri-sec-butylborohydride, sodium tri-sec-butylborohydride, lithium trisiamylborohydride, potassium trisiamylborohydride, potassium triphenylborohydride and lithium triphenylborohydride.

4. A method according to claim 3, wherein the hindered organoborane is lithium tri-sec-butylborohydride.

5. A method according to claim 1, wherein the molar ratio of the predominant sapogenin obtained to the alternative 3-epimer, is at least about 10:1.

6. A method according to claim 5, wherein the ratio is at least about 15:1.

7. A method according to claim 1, when performed in an organic solvent selected from tetrahydrofuran, toluene, tert-butyl methyl ether, diethoxymethane, 1,4-dioxan, 2-methyltetrahydrofuran and any mixture thereof.

8. A method according to claim 7, wherein the organic solvent consists essentially of tetrahydrofuran.

9. A method according to claim 7, wherein the organic solvent consists essentially of toluene.

10. A method according to claim 7, wherein the organic solvent consists essentially of 1,4-dioxan.

11. A method according to claim 7, wherein the organic solvent consists essentially of 2-methyltetrahydrofuran.

12. A method according to claim 1, wherein the sapogenin is selected from sarsasapogenin, smilagenin, and esters thereof.

13. A method according to claim 1, wherein the 3-keto, 5β-H steroidal sapogenin starting material is prepared by heterogeneous catalytic hydrogenation of a corresponding $\Delta^4$, 3-keto steroidal sapogenin to convert the $\Delta^4$, 3-keto steroidal sapogenin at least predominantly to the said 5β-H,3-ketone.

14. A method according to claim 13, wherein the heterogeneous catalytic hydrogenation is performed using hydrogen and a palladium catalyst in an organic solvent.

15. A method according to claim 14, wherein the palladium catalyst is present on a support.

16. A method according to claim 13, wherein the $\Delta^4$, 3-keto steroidal sapogenin is diosgenone.

17. A method according to claim 16, wherein the diosgenone is obtained by oxidation of diosgenin.

18. A method for the synthesis of smilagenin, comprising catalytic hydrogenation of diosgenone followed by reduction of the resulting 3-keto, 5β-H steroidal sapogenin using a hindered organoborane.

19. A method according to claim 2, wherein the hindered organoborane is an alkali metal tri-alkyl or tri-aryl borohydride reducing agent.

20. A method according 18, wherein the 3-keto-5β-H steroidal sapogenin is prepared by heterogeneous catalytic hydrogenation of a corresponding $\Delta^4$, 3-keto steroidal sapogenin to convert the $\Delta^4$, 3-keto steroidal sapogenin at least predominantly to the said 5β-H, 3-ketone.

21. A method according to claim 20, wherein the $\Delta^4$, 3-keto steroidal sapogenin is diosgenone, which is obtained by oxidation of diosgenin.

22. A method according to claim 1, wherein a sapogenin initially formed is subsequently converted to a pro-drug form thereof or to another physiologically acceptable form thereof.

23. A method according to claim 1, wherein the β-OH of $R_{10}$ in the sapogenin initially formed is converted to a β-O-linked sugar group.

24. A method according to claim 1, wherein the β-OH of $R_{10}$ is the sapogenin initially formed and subsequently converted to an β-organic ester group.

* * * * *